United States Patent
Lin et al.

(10) Patent No.: US 10,555,984 B2
(45) Date of Patent: Feb. 11, 2020

(54) **METHOD FOR INCREASING EXPRESSION OF *PDPRD* GENE BY USING PEANUT SKIN EXTRACT**

(71) Applicant: TCI CO., LTD., Taipei (TW)

(72) Inventors: Yung-Hsiang Lin, Taipei (TW); Chih-Hsiu Yu, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 15/957,630

(22) Filed: Apr. 19, 2018

(65) Prior Publication Data

US 2018/0303893 A1    Oct. 25, 2018

Related U.S. Application Data

(60) Provisional application No. 62/488,336, filed on Apr. 21, 2017.

(51) Int. Cl.
*A61K 36/48* (2006.01)
(52) U.S. Cl.
CPC .......... *A61K 36/48* (2013.01); *A61K 2236/00* (2013.01)

(58) Field of Classification Search
None
See application file for complete search history.

(56) References Cited

U.S. PATENT DOCUMENTS 6,258,361 B1 * 7/2001 Yoshihara .............. A61K 36/48
424/195.11

OTHER PUBLICATIONS

Taha (Life Science Journal (2012), vol. 9, No. 2, pp. 207-215).*
Acun, Tolga, et al., "*PTPRD* is Homozygously Deleted and Epigenetically Downregulated in Human Hepatocellular Carcinomas," *OMICS*, 19(4), pp. 220-229 (2015).
Wang, Dandan, et al., "Reduced Expression of *PTPRD* Correlates with Poor Prognosis in Gastric Adenocarcinoma," *PLOS ONE*, 9(11), 17 pages (Nov. 20, 2014).

* cited by examiner

*Primary Examiner* — Susan Hoffman
(74) *Attorney, Agent, or Firm* — Christensen, Fonder, Dardi & Herbert PLLC

(57) ABSTRACT

A method for increasing the expression of PTPRD gene is provided, wherein the method comprises administering to a subject in need an effective amount of a peanut skin extract. The method is effective in preventing or treating diseases related to PTPRD gene.

3 Claims, 1 Drawing Sheet

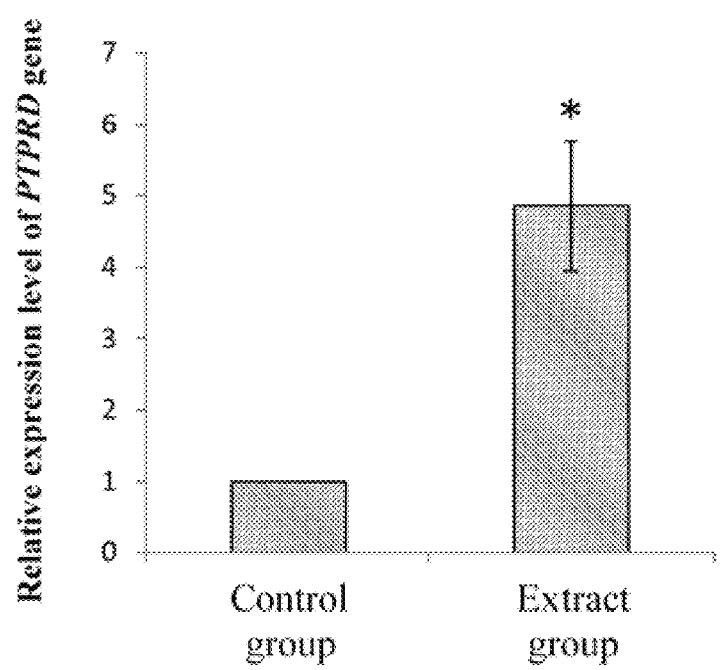

METHOD FOR INCREASING EXPRESSION OF *PDPRD* GENE BY USING PEANUT SKIN EXTRACT

FIELD OF THE INVENTION

The present invention relates to the uses of a peanut skin extract, and especially to the uses of a water extract of peanut skin, wherein the uses include using the extract for preventing or treating diseases related to the PTPRD gene.

BACKGROUND OF THE INVENTION

Peanut (*Arachis hypogaea*) is a common agricultural crop and one of the primary oil crops, and can be manufactured into various processed foods such as peanut candy, peanut butter, peanut oil, etc. It is known that peanuts have nutrient components such as carbohydrates, lipids, proteins, vitamin B, and minerals. Lipids compose 50% of peanuts and are primarily unsaturated lipid acids that are effective in decreasing the amount of cholesterols in human body, and preventing arteriosclerosis and cardiovascular diseases. Thus, it is healthy to eat an appropriate amount of peanut. However, the aforementioned components and effects all are linked with the fruits of peanuts. The skins of peanuts are usually regarded as useless waste.

Inventors of the present invention surprisingly discovered that the peanut skin extract is effective in increasing the expression of PTPRD gene. It is known that PTPRD gene is a tumor suppressor gene. Its deletion, mutation or low expression are found in various human tumors, such as liver cancer and gastric cancer. Based on the discovery of inventors of the present invention, the peanut skin, which was known as waste, can be used for preventing or treating liver cancer and gastric cancer.

SUMMARY OF THE INVENTION

One objective of the present invention is to provide a use of a peanut skin extract in the manufacture of a composition, wherein the composition is used for increasing the expression of PTPRD gene. Preferably, the extract is obtained by extracting the peanut skin with a polar solvent. More preferably, the extract is obtained by extracting the peanut skin with water.

The composition provided in accordance with the present invention is a pharmaceutical composition or a food composition, wherein the pharmaceutical composition is used for at least one of preventing liver cancer, preventing gastric cancer, treating liver cancer, and treating gastric cancer. Preferably, the pharmaceutical composition is provided in the form for oral administration, intravenous injection, subcutaneous injection, or a combination thereof.

The food composition provided in accordance with the present invention is preferably a health food, a dietary supplement, a functional food, a nutritional supplement, or a special nutritional food.

Another objective of the present invention is to provide a method for increasing the expression of PTPRD gene, comprising administering to a subject in need an effective amount of a peanut skin extract. The method of the present invention is for at least one of preventing liver cancer, preventing gastric cancer, treating liver cancer, and treating gastric cancer. In the method of the present invention, the peanut skin extract can be administered to a subject in need as a form of the pharmaceutical composition or food composition as described above.

The detailed technology and preferred embodiments implemented for the present invention will be described in the following paragraphs for persons skilled in the art to well appreciate the features of the claimed invention.

BRIEF DESCRIPTION OF THE DRAWINGS

FIG. 1 shows the effect of the peanut skin extract in increasing the expression level of PTPRD gene, wherein the HepG2 cells in "control group" were cultivated with a medium free of peanut skin extract for 48 hours; and those in the "extract group" were cultivated with a medium externally added with peanut skin extract for 48 hours (* represents a result that is significantly different from that of the control group, p<0.05).

DESCRIPTION OF THE PREFERRED EMBODIMENT

The following paragraphs will describe some of the embodiments of the present invention in detail. However, without departing from the spirit of the present invention, the present invention may be embodied in various embodiments and should not be limited to the embodiments described in the specification.

Unless otherwise indicated herein, the expression "a," "an," "the," or the like recited in the specification of the present invention (especially in the claims) are intended to include both the singular and plural forms. The term "prevent" or "preventing" recited in this specification refers to inhibiting or avoiding a particular condition of illness from breaking out, maintaining good health in a sensitive subject or establishing the ability of a sensitive subject to tolerate diseases. The term "treat", or "treating" recited in this specification should not be construed as treating a subject until the subject is completely recovered, but should include maintaining the progression or symptoms of the diseases in a substantially static state, increasing the recovery rate of a subject, alleviating the severity of a particular condition of illness, or enhancing the quality of life of a patient. The term "subject" recited in this specification refers to a mammalian, including human and non-human animals.

PTPRD gene is a tumor suppressor gene and its deletion, mutation or low expression are found in various human tumors, such as liver cancer and gastric cancer. These can be noted from such as "PTPRD is homozygously deleted and epigenetically downregulated in human hepatocellular carcinomas. *OMICS: A Journal of Integrative Biology* 19(4): 220-9 (2015)," and "Reduced Expression of PTPRD Correlates with Poor Prognosis in Gastric Adenocarcinoma. *PLOS ONE.* 9(11): e113754 (2014)", which are entirely incorporated hereinto by reference. Therefore, if the expression of PTPRD gene can be increased effectively, the effects of preventing or treating liver cancer and gastric cancer can be provided.

Inventors of the present invention discovered that the peanut skin extract is effective in increasing the expression of PTPRD gene. Therefore, the present invention relates to the uses of peanut skin extract in increasing the expression of PTPRD gene, including the use of peanut skin extract in the manufacture of a composition, and a method for using the peanut skin extract, wherein the method comprises administering to a subject in need an effective amount of a peanut skin extract to increase expression of PTPRD gene in the subject.

The peanut skin extract adopted in accordance with the present invention can be provided by extracting the peanut skin with a polar solvent, wherein the polar solvent is water, alcohols (e.g., C1-C4 alcohols), or combinations thereof. Moreover, the amount of solvent used in the extraction is not critical and is generally capable of evenly dispersing the material to be extracted. For example, in the extraction step, the extraction solvent and peanut skin could be adopted at a volume ratio of 20~1:1 (extraction solvent: peanut skin). Optionally, operations such as stirring or low-temperature ultrasonic vortex could be performed during the extraction. The peanut skin could also be crushed prior to conducting the extraction to enhance the extraction efficiency.

In some embodiments of the present invention, the extraction was carried out by mixing water and peanut skin at a volume ratio of 10:1 (water: peanut skin), and then subjecting the mixture to an ultrasonic vortex at a temperature of 20° C. to 30° C. for 30 to 60 minutes. Furthermore, the peanut skins were obtained by peeling the fresh peanuts at a temperature of no more than 90° C.

The peanut skin extract adopted in accordance with the present invention could be the liquid directly obtained from extraction (i.e., "original extract liquid"), or the liquid obtained from further treating the original extract liquid with one or more optional steps such as filtration, sterilization, concentration and dilution so as to facilitate the use of the extract. For example, a concentrated liquid or powder with carry or storage convenience could be obtained from the extract liquid via a procedure such as vacuum concentration, concentration-drying, spray-drying, or freeze-drying. In one embodiment of the present invention, the extract liquid thus obtained was subjected to a vacuum concentration at a temperature of 45° C. to 70° C., and then spray-dried to remove water and provide a peanut skin extract as needed.

The composition provided in accordance with the present invention is a pharmaceutical composition or a food composition, wherein the pharmaceutical composition can be used for preventing or treating liver or gastric cancer.

Depending on the desired purpose, the pharmaceutical composition in accordance with the present invention could be provided in any suitable form without any special limitations. For example, the pharmaceutical compositions could be administered to a subject in need by an oral or parenteral (e.g., intravenous or subcutaneous) route. Depending on the form and purpose, suitable carriers could be chosen and used to provide the pharmaceutical composition. Examples of the carriers include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a dosage form for oral administration, the pharmaceutical composition provided in accordance with the present invention could comprise any pharmaceutically acceptable carrier that will not adversely affect the desired effects of the active ingredients (i.e., peanut skin extract), such as water, saline, dextrose, glycerol, ethanol or its analogs, cellulose, starch, sugar bentonite, and combinations thereof. The pharmaceutical composition could be provided in any suitable form for oral administration, such as in the form of a tablet (e.g., sugar-coated tablet), a pill, a capsule, granules, a pulvis, a fluid extract, a solution, a syrup, a suspension, a tincture, etc.

As a form of injection or drip suitable for subcutaneous injection or intravenous injection, the pharmaceutical composition provided in accordance with the present invention can comprise one or more ingredient(s), such as an isotonic solution, a salt-buffered saline (e.g., phosphate-buffered saline or citrate-buffered saline), a hydrotropic agent, an emulsifier, a 5% sugar solution, and other carriers to provide the pharmaceutical composition as an intravenous infusion, an emulsified intravenous infusion, a powder for injection, a suspension for injection, or a powder suspension for injection, etc. Alternatively, the pharmaceutical composition can be prepared as a pre-injection solid. The pre-injection solid could be provided in a form which is soluble in other solutions or suspensions, or in an emulsifiable form. A desired injection is provided by dissolving the pre-injection solid in other solutions or suspensions or emulsifying it prior to being administered to a subject in need.

Depending on the need, age, body weight, and health conditions of the subject, the pharmaceutical composition provided in accordance with the present invention could be administered at various frequencies, such as once a day, multiple times a day, or once every few days, etc. The ratio of amount of peanut skin extract in the pharmaceutical composition provided in accordance with the present invention could be adjusted depending on the requirements of practical application. In addition, the pharmaceutical composition could optionally further comprise one or more other active ingredient(s), or to be used in combination with a medicament comprising one or more other active ingredient(s), to further enhance the effects of the pharmaceutical composition, or to increase the application flexibility and application adaptability of preparation thus provided, as long as the other active ingredients do not adversely affect the desired effects of the active ingredients of the present invention (i.e., peanut skin extract).

Optionally, the pharmaceutical composition or food composition provided in accordance with the present invention could further comprise a suitable amount of additives, such as a flavoring agent, a toner, or a coloring agent for enhancing the palatability and the visual perception of the pharmaceutical composition or food composition, and/or a buffer, a conservative, a preservative, an antibacterial agent, or an antifungal agent for improving the stability and storability of the pharmaceutical composition or food composition.

The food combination provided in accordance with the present invention can be a health food, a dietary supplement, a functional food, a nutritional supplement food or a special nutritional food, and can be manufactured as dairy products, meat products, breadstuff, pasta, cookies, troche, capsules, fruit juices, tea products, sports beverages, nutrient beverages, etc., but is not limited thereby. Preferably, the food composition provided in accordance with the present invention is a health food.

Depending on the need, age, body weight, and health conditions of the subject, the food composition provided in accordance with the present invention could be taken at various frequencies, such as once a day, multiple times a day, or once every few days, etc. The amount of peanut skin extract in the food composition provided in accordance with the present invention could also be adjusted, preferably to the amount that should be taken daily, depending on the specific population.

The recommended daily dosage, use standards and use conditions for a specific population (e.g., cancer patients, pregnant woman, etc.), or the recommendations for a use in combination with another food product or medicament could be labeled on the exterior package of health food, dietary supplement, functional food, nutritional supplement food and/or special nutritional food provided in accordance with the present invention. Thus, it is suitable for the users to take the health food, dietary supplement, functional food, nutritional supplement food and/or special nutritional food by him- or herself safely and securely without the instructions of a doctor, pharmacist or related executive. In the food combination provided in accordance with the present invention, the type and uses in related applications of peanut skin extract are all in line with the above descriptions.

The present invention also provides a method for increasing the expression of PTPRD gene, comprising administering a subject in need an effective amount of a peanut skin extract. The aforementioned "subject in need" refers to a subject whose PTPRD gene is deficient, mutated, or expressed at low levels. Preferably, the method is for at least one of preventing liver cancer, preventing gastric cancer, treating liver cancer, and treating gastric cancer. The peanut skin extract adopted in accordance with the method of the present invention could be administered to the subject in need as the form of a composition. The applied type, applied route, applied form, applied frequency, and uses in the related applications of the composition are all in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Example

A. Preparation of Peanut Skin Extract

The peanuts Tainan No. 11 (habitat: Beigang, Yunlin, Taiwan; purchased from Da-Jia peanut and water caltrop wholesaler, New Taipei city, Taiwan) were shelled and sieved to remove the clod and defectives, and then, the peanut fruits were peeled by a peeling machine (at a temperature of no more than 90° C.). Then, the peanut skins thus obtained were crushed to provide a peanut skin material.

The peanut skin material was subjected to the following operations to provide a peanut skin extract:
1. Mixing the peanut skin material with water evenly at a volume ratio of 1:10 (peanut skin material: water) to provide a mixture, then subjecting the mixture to an ultrasonic extraction at a temperature of 25° C. for 45 minutes to provide a crude extract liquid;
2. Filtering the crude extract liquid to provide a filtrate;
3. Centrifuging the filtrate at a rotor speed of 4,800 rpm, and collecting the supernatant;
4. Concentrating the supernatant via a vacuum concentration at a temperature of 45° C. to 70° C. until the volume of supernatant was decreased to one-tenth of its original volume to provide a concentrated extract; and
5. Sterilizing the concentrated extract via an ultra-high-temperature processing (UHT), and then spray-drying the same to provide a dried powder.

Example 1: Effects of Peanut Skin Extract in Increasing Expression of PTPRD Gene The Dulbecco's Modified Eagle's Medium (DMEM; purchased from Gibco) was evenly mixed with fetal bovine serum (FBS; purchased from Gibco) (DMEM: FBS=9:1 in volume) to provide the cell medium used in this example (hereinafter referred to as "DMEM medium").

2 mL of DMEM medium was added into each well of a 6-well plate, and then, HepG2 cells (a human hepatocellular carcinoma cell line; purchased from ATCC; product no. HB-8065™) were seeded ($1 \times 10^5$ cells/well) into each well. The plate was placed under 37° C. for conducting a cultivation for 24 hours. Then, the cells were divided into control group and extract group, and respectively subjected to the following procedures:
1. Control group: the DMEM medium was refreshed and the cells were continuously cultivated for 48 hours; and
2. Extract group: the DMEM medium was refreshed, and the powder obtained from [Preparation example A] was externally added into the medium at an amount of 0.75 mg (based on the dry weight of powder) per milliliter of medium, and the cells were continuously cultivated for 48 hours.

The cells of each group were harvested and subjected to an RNA extraction with an RNA extraction kit (purchased from Geneaid). The RNA of each group was reverse transcribed into cDNA with a SuperScript™ Reverse Transcriptase kit (purchased from Invitrogen). Then, the cDNA of each group was subjected to qPCR (quantitative polymerase chain reaction) by an ABI StepOne Plus™ System and a KAPA SYBR FAST qPCR Kit (2×) (purchased from KAPA Biosystems), to determine the expression level of PTPRD gene in the cells of each group.

The above experimentation was repeated thrice, and the results of the three experimentations were averaged. Then, the result of control group was used as a basis (i.e., the expression level of PTPRD gene in the cells of control group was set as 1-fold) to calculate the relative gene expression level in the cells of the extract group. The results are shown in FIG. 1.

As shown in FIG. 1, in comparison with the control group, the expression level of PTPRD gene in the cells of extract group was significantly increased. This result indicates that the peanut skin extract of the present invention can effectively increase the expression of PTPRD gene, and thus, can be used for at least one of preventing liver cancer, preventing gastric cancer, treating liver cancer, and treating gastric cancer.

What is claimed is:

1. A method for preventing or treating hepatocellular carcinoma, consisting of administrating to a subject in need an effective amount of a composition consisting of a peanut skin extract and a carrier, wherein the extract is obtained by extracting the peanut skin with water.

2. The method as claimed in claim 1, wherein the composition is administered to the subject by oral administration, intravenous injection, subcutaneous injection, or a combination thereof.

3. The method as claimed in claim 1, wherein the method is for preventing or treating hepatocellular carcinoma by increasing expression of PTPRD gene.

* * * * *